(12) United States Patent
Mioskowski et al.

(10) Patent No.: US 7,517,587 B2
(45) Date of Patent: Apr. 14, 2009

(54) MACROMOLECULES AUTO-ASSEMBLED AND PHOTOPOLYMERISED AROUND CARBON NANOTUBES, A METHOD FOR PRODUCTION AND APPLICATION THEREOF

(75) Inventors: Charles Mioskowski, Strasbourg (FR); Stéphane Rickling, Hirtzfelden (FR); Patrick Schultz, Fegersheim (FR)

(73) Assignees: Centre National de la Recherche Scientifique (C.N.R.S.), Paris Cedex (FR); Universite Louis Pasteur, Strasbourg (FR)

( * ) Notice: Subject to any disclaimer, the term of this patent is extended or adjusted under 35 U.S.C. 154(b) by 0 days.

(21) Appl. No.: 10/553,260

(22) PCT Filed: Apr. 13, 2004

(86) PCT No.: PCT/FR2004/000906

§ 371 (c)(1),
(2), (4) Date: Nov. 8, 2006

(87) PCT Pub. No.: WO2004/092231

PCT Pub. Date: Oct. 28, 2004

(65) Prior Publication Data

US 2007/0184267 A1 Aug. 9, 2007

(30) Foreign Application Priority Data

Apr. 10, 2003 (FR) .................. 03 04492

(51) Int. Cl.
*B01J 13/04* (2006.01)
*B05D 3/14* (2006.01)

(52) U.S. Cl. ............... 428/407; 427/213.3; 427/213.34; 427/226; 977/756

(58) Field of Classification Search ................ 428/403, 428/407; 427/213.3, 213.34, 226; 977/756
See application file for complete search history.

(56) References Cited

U.S. PATENT DOCUMENTS 6,426,134 B1  7/2002  Lavin et al.
6,613,875 B1 * 9/2003  Ghadiri ....................... 530/321
6,632,497 B2 * 10/2003 Shimizu et al. ............. 428/36.9
6,656,712 B1 * 12/2003 Balavoine et al. ........... 435/176
6,878,361 B2 * 4/2005  Clarke et al. ................ 423/461
7,244,499 B2 * 7/2007  Sugiyama et al. ........... 428/407
7,341,738 B2 * 3/2008  Semple et al. .............. 424/450
2005/0214356 A1 * 9/2005  Joyce ........................ 424/450

FOREIGN PATENT DOCUMENTS

| JP | 2000-53407 | 2/2000 |
| JP | 2004-82663 | 3/2004 |
| WO | 99/57564 | 11/1999 |
| WO | 99/61912 | 12/1999 |
| WO | 02/44336 A2 | 6/2002 |

OTHER PUBLICATIONS

International Search Report of PCT/FR2004/000906, mailed Oct. 4, 2004.

* cited by examiner

*Primary Examiner*—H. (Holly) T Le
(74) *Attorney, Agent, or Firm*—Nixon & Vanderhye P.C.

(57) ABSTRACT

The invention relates to macromolecules auto-assembled and photopolymerised around carbon nanotubes. Said macromolecules are essentially formed from rings of lipid compounds, polymerised about the nanotubes, said polymerised compounds being obtained from lipid molecules with one or two chains A, bonded to a group Z where A is a chain, $CH_3-(CH_2)_m-C\equiv C-C\equiv C-(CH_2)_n-$, where n and m, independently=whole numbers from 1 to 16 and Z is a polar head group embodied by a $-COOH$, $-CO-NH-Y$, $-NH_2$ or $N^+(R)_3$, where R is an alkyl with $C_1$, to $C_4$ and Y is a $-(CH_2)_4-C(R_1)-N(CH_2-COOH)_2$ group with R=H, or a COOH group, where A is a single lipid chain or a group of structure (I) or (II), where R2=a COOH, or $-CO-NH-Y_1$ group with $Y_1=$a $-(CH_2)_4-C(R_3)-N(CH_2COOH)_2$ group with $R_3=$H or a COOH group, where Z and $R_2$ can also be neutral polar head groups of the sugar or polysaccharide type. The above is of application particularly to the protection and purification of nanotubes, as a hydrophobic molecule or membrane protein vector or as a molecular motor.

15 Claims, No Drawings

MACROMOLECULES AUTO-ASSEMBLED AND PHOTOPOLYMERISED AROUND CARBON NANOTUBES, A METHOD FOR PRODUCTION AND APPLICATION THEREOF

This application is the US national phase of international application PCT/FR2004/000906, filed 13 Apr. 2004, which designated the U.S. and claims priority of FR 03 04 492, filed 10 Apr. 2003, the entire contents of each of which are hereby incorporated by reference.

The subject of the invention is photopolymerized macromolecules self-assembled around carbon nanotubes, a method for preparing them and their applications.

Since their discovery at the beginning of the 1990s by Iijima (Nature 354, 56 (1991)), nanotubes, and especially carbon nanotubes, have aroused increasing interest because of their physical, electronic or thermal properties. Most applications require a very high level of purity of the nanotubes, and many purification methods have been described, whether by oxidation, by filtration or by chromatography. Very often, after these processes, the nanotubes are damaged (oxidation, chipped-off ends, etc) or their graphitic structure is modified (covalent functionalization on the ends or the sidewalls of the tubes), this sometimes very substantially impairing their properties.

There is therefore an interest in having an effective and nondestructive purification method.

Studies by the inventors in this field have shown that certain compounds can self-organize around nanotubes by forming rings and thus protect them from any damage when they are being handled. Advantageously, these compounds may be detached from the nanotubes and recovered for useful applications, the nanotubes then being obtained with a very high level of purity.

The object of the invention is therefore to provide novel compounds that can be used for protecting nanotubes.

The invention also relates to a method of purifying nanotubes employing these compounds.

The object of the invention, according to yet another aspect, is to provide novel structures with self-assembly of said compounds around nanotubes and their applications, especially for the protection and purification of nanotubes, or else the vectorization of active substances.

The novel structures with macromolecules self-organized around nanotubes are characterized in that they are essentially formed from rings of polymerized lipid compounds surrounding the nanotubes, these polymerized compounds being obtained from lipid compounds comprising one or two chains A linked to a group Z:

A representing a $CH_3-(CH_2)_m-C\equiv C-C\equiv C-(CH_2)_n-$ chain;

n and m, which are the same or different, being integers from 1 to 16; and

Z representing a polar head formed by a $-COOH$, $-CO-NH-Y$, $-NH_2$ or $N^+(R)_3$ group, R being a $C_1$ to $C_4$ alkyl and Y being a $-(CH_2)_4-C(R_1)-N(CH_2-COOH)_2$ radical, with $R_1$ representing H or a COOH radical if A represents a single lipid chain, or a group of the following structure:

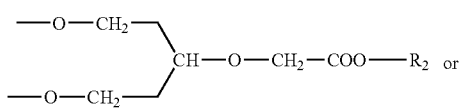

-continued

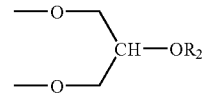

where $R_2$ represents a $-COOH$ or $-CO-NH-Y_1$ group, $Y_1$ being a $-(CH_2)_4-C(R_3)-N(CH_2-COOH)_2$ radical and where $R_3$ represents H or a COOH radical;

or Z or $R_2$ may also be hydrophilic or neutral polar heads, of the sugar or polysaccharide type.

Preferred polymerizable lipid compounds are amine lipids of formula:

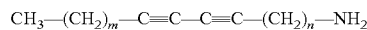

or quaternary ammoniums of formula:

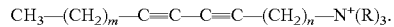

Other preferred polymerizable lipid compounds are two-chain acid lipids, that is to say with two chains A attached to Z.

Yet other compounds are lipids functionalized by a chelating group, such as nitrilotriacetic acid (NTA) or iminodiacetic acid (IDA).

The invention also relates to a method of obtaining the structures defined above, characterized in that it comprises the steps consisting in:

bringing the raw nanotubes into contact with a solution of lipids so as to form a stable suspension;

polymerizing the lipids, which are self-organized around the nanotubes; and recovering the nanotubes coated with rings formed by the polymerized lipids.

Advantageously, the raw nanotubes are sonicated in the lipid solution.

In the method of the invention, these lipids are dissolved in a buffered aqueous medium advantageously containing a detergent. As detergent, mention may be made of sodium dodecyl sulfate (SDS).

After sonification, the detergent is removed by dialysis.

The suspension of nanotubes in the aqueous buffer is subjected to a treatment for polymerizing the lipids.

Ultraviolet irradiation is employed.

In one way of implementing the invention, the structures obtained are subjected to a treatment for separating the nanotubes surrounded by polymerized lipid rings from all the impurities contained in the nanotube synthesis medium.

This step is carried out for example by size exclusion chromatography.

Stationary phases formed by silica of controlled porosity, such as the product sold under the name CPG (controlled pore glass) by Millipore Corp., have proved to be satisfactory. One or more purification steps may be carried out and the porosity advantageously modified according to the purification step. Thus, nanotubes of high purity are obtained.

It is also possible to remove the rings by applying an electric field, for example in an electrophoresis device.

The nanotubes surrounded by polymerized macromolecules thus obtained have advantageous properties in many applications.

Nanotubes surrounded by photopolymerized hemimicelles allow, in particular, controlled shortening of the tubes by sonification.

It is known that single-walled nanotubes are sensitive to strong sonification and that prolonged exposure to ultrasound greatly degrades the tubes, essentially by a phenomenon whereby the ends of the nanotubes are chipped off.

Likewise, it has been observed that the sidewalls of the nanotubes are greatly damaged after intense sonification, which disturbs the graphitic structure of the nanotubes and impairs their electronic properties.

It turns out that the single-walled nanotubes of the invention, when surrounded by polymerized macromolecules, allow controlled nanotube shortening.

Specifically, the inventors have observed that, by subjecting specimens of single-walled nanotubes covered with polymerized lipids, as described above, to a sonification treatment, it is possible to cut the nanotubes and achieve, for example, mean sizes of around 400 nm after 2 hours of sonification.

As illustrated in the examples, it is thus possible to obtain single-walled nanotubes cut to similar sizes in the form of isolated tubes or small bundles, which shows that the cutting does not take place by chipping off the ends, but rather by breaking the nanotubes into two.

The lipid polymerized on the surface of the nanotubes therefore serves to protect them.

The ring-shaped polymeric species of the invention that have been detached from the carbon nanotubes by electrophoresis constitute novel vectors for hydrophobic molecules or membrane proteins, since the inside of these rings has a membrane bilayer structure.

As indicated above, the macromolecules formed from polymerized lipids on the surface of the nanotubes are hydrophobic in their internal part and hydrophilic in their external part.

They therefore constitute useful vectors for hydrophobic molecules in aqueous media.

The subject of the invention is therefore the application of polymeric rings, detached from the nanotubes, as vectors for hydrophobic substances.

Hydrophobic substances will tend, when they are brought into contact with said polymerized macromolecules, to be placed on the inside of the hydrophobic pocket presented by the polymerized lipids. The latter are soluble in aqueous medium because of their hydrophilic external part and the hydrophobic substance/lipid assembly will therefore also be soluble.

Each application uses the nanotubes for manufacturing transporters for molecules that are water-insoluble, particularly hydrophobic medicaments and proteins.

Using lipids of appropriate size, it is possible to provide coatings that mimic the cell membrane, the polymerized macromolecules around the nanotubes being able to be likened to lipid bilayers.

With lipid sizes of the order of magnitude of that of the lipids of a cell membrane, and nanotubes of suitable diameter, the invention provides structures whose covering rings can be used to dissolve membrane proteins. By bringing membrane proteins, in aqueous medium, into contact with polymerized lipid rings according to the invention, the hydrophobic part of the membrane proteins comes into contact with the inside of the rings. The macromolecule/protein complex is then soluble in aqueous phase, allowing membrane proteins to be dissolved without having to use detergents, which would risk damaging or denaturing them.

According to another aspect of great interest, the subject of the invention is the application of single-walled and multi-walled nanotubes as molecular motors.

The nanotubes employed comprise at most a few polymerized lipid rings, preferably a single ring, and are subjected to an alternating or non-alternating electric field so as to move the ring or rings along the nanotube.

The novel structures of the invention with self-organized macromolecules around the nanotubes are also useful for the vectorization of substances in general, allowing specific or nonspecific delivery thereof. Thus, they are very useful in various fields, especially in pharmacy for encapsulating active principles of medicaments, or in cosmetics and perfumery, for the vectorization of fragrances, essential oils and the like, or for the encapsulation of various active substances such as pheromones. Advantageously, these structures can be used in standard liposome applications.

Other features and advantages of the invention will be given in the examples that follow. Transmission electron microscope micrographs of structures and nanotubes according to the invention were produced of a raw single-walled nanotube specimen and to a specimen after a $2^{nd}$ purification step;

a raw multi-walled nanotube specimen and to a specimen after a $2^{nd}$ purification step; and single-walled nanotubes cut after strong sonification for one hour.

EXAMPLE 1

Method of Obtaining Structures According to the Invention

A specimen of raw single-walled or multi-walled nanotubes, whatever the method of synthesis, was sonicated for 5 minutes in an NTA (11.8) lipid solution (lipid with nitrilotriacetic functionality) with a concentration of 1 mg/ml of Tris (pH 8) buffer containing 1% SDS. After sonification, the nanotubes were all in the form of a stable suspension in the aqueous buffer. The detergent was removed by dialysis against Tris without SDS, for 48 h, changing the Tris every 12 h. Once the dialysis had been completed, the lipid was polymerized, which self-organized around the nanotubes, by irradiating the specimen with UV ($\lambda$=254 nm) for 1 h and the structures formed were recovered.

EXAMPLE 2

Method of Purifying Nanotubes

The technique of size exclusion chromatography was used with CPG as stationary phase, CPG being sold by Millipore Corp. (Lincoln Park, N.J., USA).

A first purification step was carried out with CPG 3000 Å having a mean pore size of 300 nm. This stationary phase was placed in a 14 cm×0.7 cm column and conditioned with a 0.25% aqueous SDS solution.

0.5 ml of the suspension (1 mg/ml) of irradiated single-walled or multi-walled nanotubes was deposited on the column and eluted with 0.25% aqueous SDS solution. The eluant flux was set at about 10 ml/h. After a dead volume of 4 ml, six 2 ml fractions were collected and observed under a transmission electron microscope (TEM).

As regards the multi-walled nanotubes, most of the tubes were observed in the first fraction with a few impurities. The next fractions essentially contained amorphous carbon and other impurities, and a few rare nanotubes. The first fraction was then subjected to a second purification step by depositing 0.5 ml on a 14 cm×0.7 cm column containing CPG 1400 Å (mean cavity size: 140 nm). The same eluant was used, and after a dead volume of 6 ml, six 0.5 ml fractions were recovered, the eluant flux being set at about 10 ml/h. TEM observation showed that the second fraction contained pure multi-walled nanotubes, practically free of any impurity.

The same method was used to purify the single-walled nanotubes. After the first purification step on the CPG 3000 A column, 2 ml fractions were collected after a dead volume of 4 ml.

Observation under the microscope showed that the first of the six fractions contained the purest nanotubes.

The next fractions contained very few nanotubes and the great majority of impurities. The first fraction was resubjected to a further purification cycle, using a new CPG 3000 A column (dead volume: 2 ml; 0.5 ml fractions). Six fractions were recovered. Observation under the microscope showed that fractions 4 and 5 contained single-walled nanotubes with a greater than 95% purity.

The purified nanotube specimens were assembled and centrifuged until a black deposit and a translucent supernatant were obtained. The supernatant was removed and the nanotubes deposited were washed with pure water so as to remove the rest of the detergent.

After 3 minutes of sonification, the specimen was again centrifuged, the supernatant was removed and the washing/sonication and centrifugation steps were repeated 3 times.

The solid deposited after the final centrifugation was freeze-dried in order to give a dry specimen of clean nanotubes covered with polymerized lipids.

EXAMPLE 3

Method of Obtaining Nanotubes Stripped of the Lipid Polymer

The nanotubes obtained in Example 2 were heated to a temperature above 90° C. for about 14 h in Tris buffer, which destroyed the polymerized lipids. It was possible to remove the rest of the polymer by washing with an organic solvent, such as for example methanol or ethanol.

EXAMPLE 4

Method of Obtaining Polymerized Lipid Rings that can be Used as Vectors for Hydrophobic Molecules or Proteins The nanotubes surrounded with polymeric macromolecules were subjected to an electrophoresis treatment on agarose gel using an electrolyte containing a Tris-glycine buffer with 0.1% SDS. Thus, the molecular rings could be detached from the carbon nanotubes and recovered so as to be used in other applications.

EXAMPLE 5

Preparation of Nanotubes with Rings of Polymerized Macromolecules, Which can be Used as Molecular Motors A small proportion of photopolymerizable lipid was mixed with another, nonphotopolymerizable, lipid chosen from lipids that do not form mixed micelles, in aqueous solution, with the photopolymerizable lipid. A suitable nonphotopolymerizable lipid had one end slightly perfluorinated, which lipid will form micelles only with lipids of the same type but will not form mixed micelles with entirely hydrogenated lipids.

The procedure was as indicated above. Nanotubes with two types of micelle and therefore two types of ring, only one being photopolymerizable, were obtained. Given that the photopolymerizable lipids were taken in small amount compared with the other type of lipid, only very few polymerizable arrangements form on the nanotubes. After irradiation by UV, the products were washed with an organic solvent, such as methanol or ethanol, so as to remove any element not polymerized around the nanotubes.

Only a few rings, preferably a single ring, therefore remained on the nanotubes, which can be used in applications as nanomotors.

EXAMPLE 6

Synthesis of the Lipid Compounds Used to Manufacture the Structures of the Invention Synthesis General acid synthesis scheme:

Scheme 1:

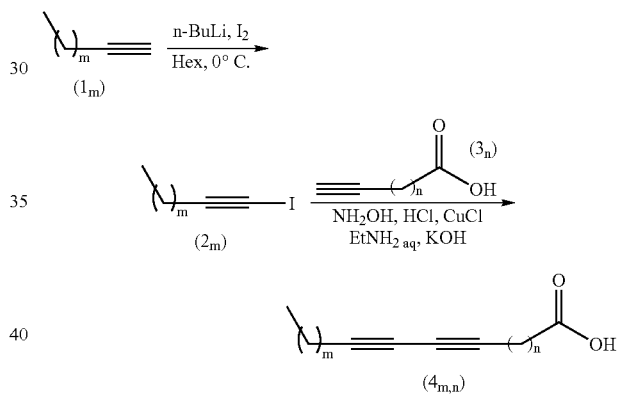

Scheme 2:

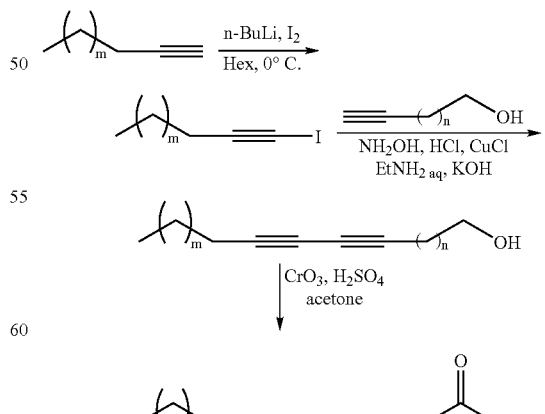

Amine lipid synthesis:
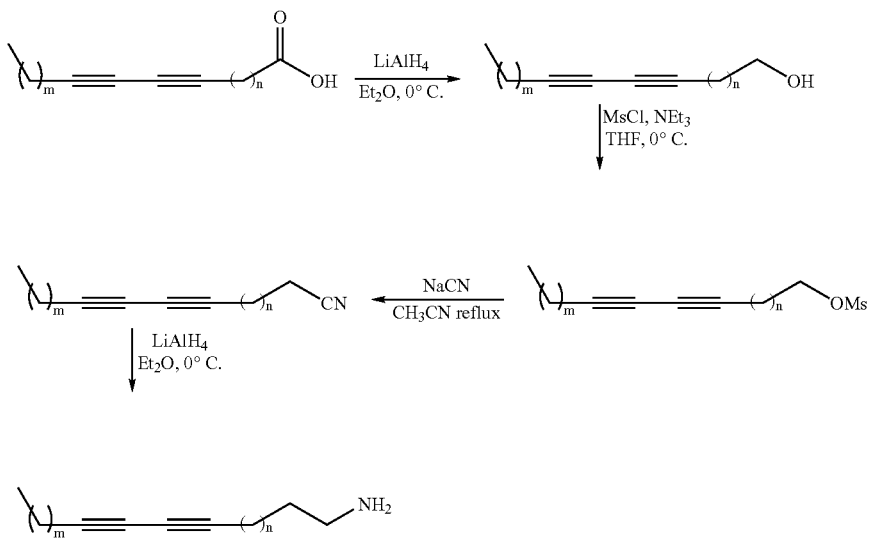
Quaternary ammonium synthesis:
Scheme 1:
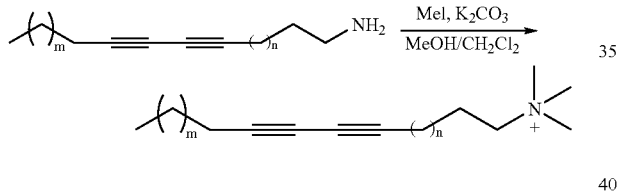
Scheme 2:
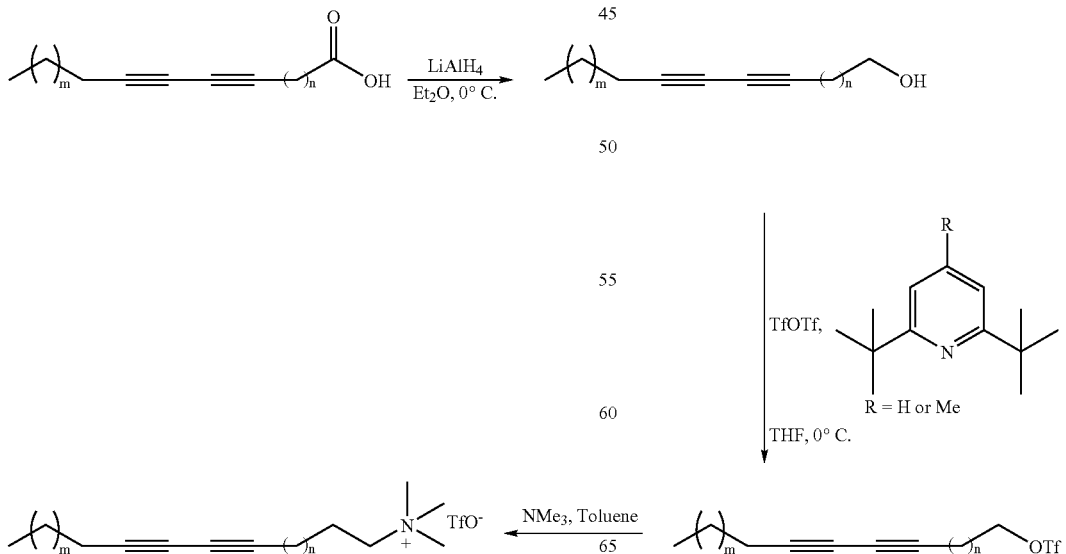

Two-chain acid lipid synthesis:
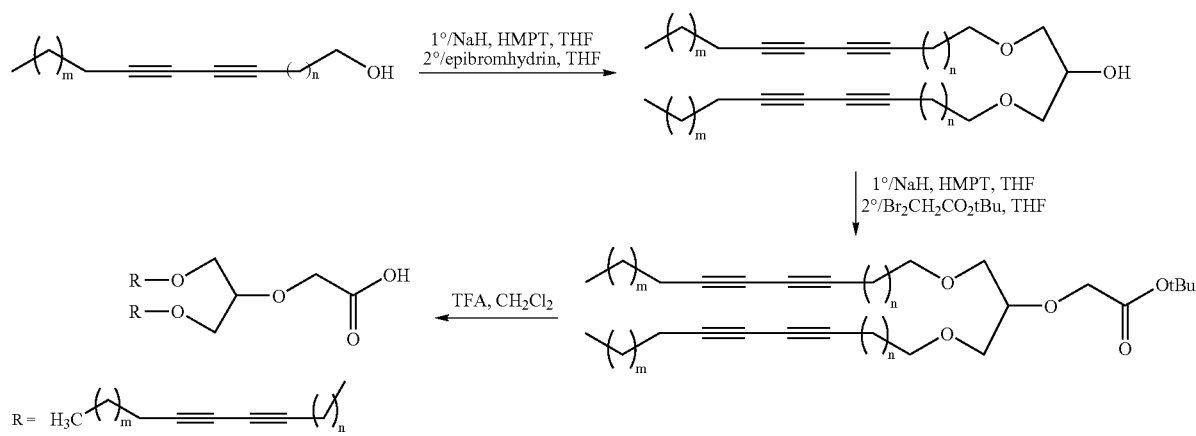
NTA lipid synthesis:
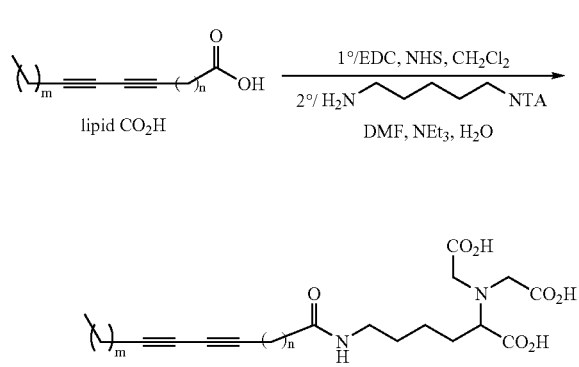
Two-chain NTA lipid synthesis:
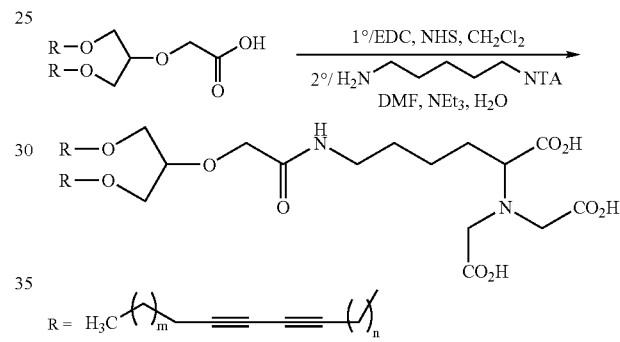
Fluorinated lipid synthesis:
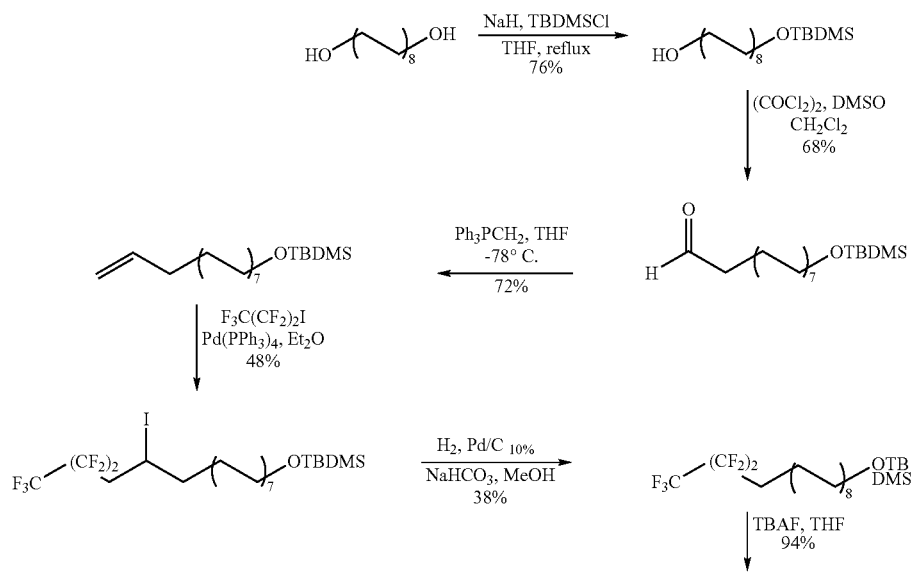

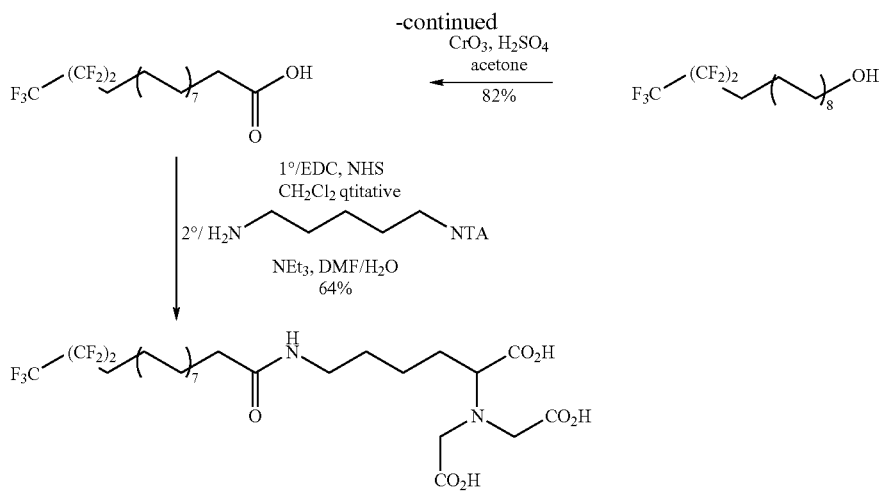

The invention claimed is:

1. A structure comprising macromolecules self-organized around carbon nanotubes, wherein said structure is essentially formed from rings of polymerized lipid compounds surrounding the carbon nanotubes, the polymerized lipid compounds comprising one chain, A, or two A chains, said one chain A or two A chains being linked to a group Z, said polymerized lipid compounds having the structure A-Z-A or A-Z, wherein:

A represents a $CH_3-(CH_2)_m-C\equiv C-C\equiv C-(CH_2)_n-$ chain, wherein n and m, which are the same or different, are integers from 1 to 16; and Z represents a polar head formed by a —COOH, —CO—NH—Y, —NH$_2$ or N$^{+(R)}{}_3$ group, R being a $C_1$ to $C_4$ alkyl and Y being a —(CH$_2$)$_4$—C(R$_1$)—N(CH$_2$—COOH)$_2$ radical, provided that if said polymerized lipid compounds contain one chain, A, then R$_1$ represents H or a COOH radical, and A further represents a group of the following structure:

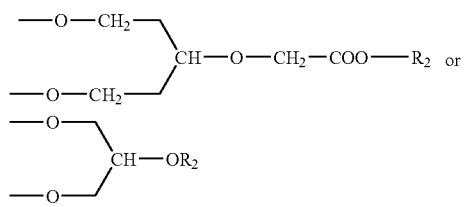

where R$_2$ represents a —COOH or —CO—NH—Y$_1$ group, Y$_1$ being a —(CH$_2$)$_4$—C(R$_3$)—N(CH$_2$—COOH)$_2$ radical and where R$_3$ represents H or a COOH radical;

or Z or R$_2$ may also be hydrophilic or neutral polar heads.

2. The structure as claimed in claim 1, characterized in that the lipid compounds to be polymerized are amine lipids of formula:

$$CH_3-(CH_2)_m-C\equiv C-C\equiv C-(CH_2)_n-NH_2.$$

3. The structure as claimed in claim 2, wherein the lipid compounds to be polymerized are functionalized by a chelating group.

4. The structure as claimed in claim 1, wherein the lipid compounds to be polymerized are quaternary ammoniums of formula:

$$CH_3-(CH_2)_m-C\equiv C-C\equiv C-(CH_2)_n-N^+(R)_3.$$

5. The structure as claimed in claim 1, wherein the lipid compounds to be polymerized are acid lipids with two chains A attached to Z.

6. The structure as claimed in claim 1, wherein the lipid compounds to be polymerized are functionalized by a neutral hydrophilic head.

7. The structure as claimed in claim 6, wherein the neutral hydrophilic head is a moiety of a sugar or polysaccharide.

8. A method of obtaining the structure as claimed in claim 1, comprising:
    bringing the raw nanotubes into contact with a solution of lipids so as to form a stable suspension;
    polymerizing the lipids, which are self-organized around the nanotubes; and
    recovering the nanotubes coated with rings formed by the polymerized lipids.

9. The method as claimed in claim 8, wherein the raw nanotubes are sonicated in a lipid solution in a buffered aqueous medium, optionally containing a detergent, the latter being subsequently removed by dialysis, and then the suspension of nanotubes in the aqueous buffer is subjected to a treatment for polymerizing the lipids.

10. A method for obtaining nanotubes protected by a polymer coating, said method comprising treating nanotubes according to the method of claim 9 and, optionally, shortening the nanotubes thus obtained through sonication.

11. A method of producing nanotubes of similar sizes comprising sonicating the structures of claim 1 to produce structures of similar sizes, and removing said polymerized lipid compounds around the nanotubes of said structures by application of an electric field or heat in order to remove said polymerized lipid compounds to produce said nanotubes of similar sizes.

12. The method as claimed in claim 11, wherein said structures of similar sizes are subjected to size exclusion chromatography.

13. The method as claimed in claim 11, wherein said heat is applied to said structures of similar sizes in a Tris buffer at a temperature above 90° C. for about 14 hours.

14. A method for obtaining vectors for hydrophobic molecules or membrane proteins, comprising:
   applying an electric field to the structures of claim 1 to detach said ring of polymerized lipid from said nanotubes, and
   recovering said polymerized lipid rings as said vectors.

15. A method of encapsulating an active principle in macromolecules comprising a lipid bilayer, said method comprising
   applying an electric field to the structures of claim 1 to detach said ring of polymerized lipid from said nanotubes to produce said macromolecules, and
   loading said macromolecules with said active principle to produce macromolecules encapsulating said active principle.

\* \* \* \* \*